(12) United States Patent
Itoh

(10) Patent No.: US 8,030,081 B2
(45) Date of Patent: Oct. 4, 2011

(54) REAGENT FOR QUANTITATIVE DETERMINATION OF SMALL, DENSE LDLS

(75) Inventor: Yasuki Itoh, Niigata (JP)

(73) Assignee: Denka Seiken Co., Ltd., Tokyo (JP)

( * ) Notice: Subject to any disclaimer, the term of this patent is extended or adjusted under 35 U.S.C. 154(b) by 0 days.

(21) Appl. No.: 12/528,929

(22) PCT Filed: Feb. 28, 2008

(86) PCT No.: PCT/JP2008/053470
§ 371 (c)(1),
(2), (4) Date: Aug. 27, 2009

(87) PCT Pub. No.: WO2008/105486
PCT Pub. Date: Sep. 4, 2008

(65) Prior Publication Data
US 2010/0035288 A1    Feb. 11, 2010

(30) Foreign Application Priority Data

Feb. 28, 2007  (JP) ................................ 2007-049533

(51) Int. Cl.
*G01N 33/92* (2006.01)
*C12Q 1/60* (2006.01)

(52) U.S. Cl. ............ 436/71; 436/13; 436/174; 436/175; 435/11; 435/19; 435/27

(58) Field of Classification Search ................ 436/8, 13, 436/17, 63, 71, 174, 175; 252/408.1; 435/11, 435/19, 26, 27
See application file for complete search history.

(56) References Cited

U.S. PATENT DOCUMENTS

| 6,194,164 B1 | 2/2001 | Matsui et al. |
| 6,794,157 B1 | 9/2004 | Sagiuchi |
| 2006/0154374 A1 | 7/2006 | Ito et al. |
| 2009/0263844 A1 * | 10/2009 | Itoh ................. 435/19 |
| 2010/0041080 A1 * | 2/2010 | Aratake et al. ............ 435/11 |

FOREIGN PATENT DOCUMENTS

| EP | 0 990 904 A1 | 4/2000 |
| EP | 1 114 870 A1 | 7/2001 |
| JP | 2001-224397 | 8/2001 |
| JP | 2003-028882 | 1/2003 |
| WO | WO-98/47005 | 10/1998 |
| WO | WO-00/17388 | 3/2000 |
| WO | WO-2004/053500 | 6/2004 |
| WO | WO-2007/026829 | 3/2007 |

OTHER PUBLICATIONS

Hirano et al., "A Novel and Simple Method for Quantification of Small, Dense LDL," Journal of Lipid Research, Nov. 2003, vol. 44, No. 11, pp. 2193-2201.
International Search Report PCT/JP2008/053470 dated Mar. 18, 2008.
Supplementary European Search Report EP 08 72 0965 dated Aug. 4, 2010.

* cited by examiner

*Primary Examiner* — Maureen Wallenhorst
(74) *Attorney, Agent, or Firm* — Stephen A. Bent; Foley & Lardner LLP

(57) ABSTRACT

A reagent for fractional measurement of small, dense LDLs without pretreatment of a specimen, which is adaptable to a rapid and convenient autoanalyzer, is provided. A method for quantitatively determining cholesterol in small, dense LDLs in a sample is further provided. The method includes first step of eliminating lipoproteins other than small, dense LDLs in a sample in the presence of cholesterol esterase and 0.05 g/L to 1.0 g/L of a surfactant that acts on the lipoproteins other than small, dense LDLs, and a second step of quantitatively determining cholesterol in small dense LDLs that remain after the first step.

10 Claims, 3 Drawing Sheets

US 8,030,081 B2

REAGENT FOR QUANTITATIVE DETERMINATION OF SMALL, DENSE LDLS

TECHNICAL FIELD

The present invention relates to a reagent for measuring cholesterol in small, dense lipoproteins (LDLs), which is important for diagnosis of arteriosclerosis.

BACKGROUND ART

Low density lipoproteins (LDLs) play a major role in cholesterol transport in the blood and are risk factors for arteriosclerosis. It is known that small, dense lipoproteins (small, dense LDLs (small-particle, low-density lipoproteins)), which are particularly small in particle size among LDLs and higher in specific gravity compared with standard LDLs, have arteriosclerosis-inducing ability at a level several-fold higher than that of normal LDLs. Increase of small, dense LDLs is one of the major risk factors for arteriosclerosis. It is clinically very important to perform a fractional measurement for such small, dense LDLs.

Examples of conventional methods for measurement of small, dense LDLs include an ultracentrifugation method, an electrophoresis method, and a method using high performance liquid chromatography. These methods are not convenient since they require expensive facilities and much time for measurement.

An example of a method for measuring small, dense LDLs using an autoanalyzer is a method (see JP Patent Publication (Kokai) No. 2003-28882 A) that involves mixing and suspending or dissolving small, dense LDLs with the use of differences in ionic strength and then measuring the small, dense LDLs with the use of differences in absorbance. However, differences in absorbance are measured based on turbidity according to such method, and thus specificity and accuracy are insufficient.

Furthermore, a method (see WO2004/053500) that involves measuring cholesterol or triglycerides in small, dense LDLs through the use of a combination of a separation agent comprising polyanions and divalent cations and a reagent adaptable for an autoanalyzer is known. This method is capable of measuring lipid components in small, dense LDLs more conveniently than an ultracentrifugation method or an electrophoresis method. Furthermore, the method is excellent in specificity and accuracy. However, the method requires pretreatment of specimens and a procedure for separating small, dense LDLs from LDLs other than such LDLs.

DISCLOSURE OF THE INVENTION

Object to be Achieved by the Invention

An object of the present invention is to provide a reagent for fractional measurement of small, dense LDLs without pretreatment of a specimen, which is adaptable to a rapid and convenient autoanalyzer.

Means to Achieve the Object

As a result of intensive studies in pursuit of the objective, the inventors discovered that, when cholesterol in a sample that contains various lipoproteins is measured using cholesterol esterase and cholesterol oxidase or cholesterol dehydrogenase, the rates of the enzymes' reaction with small, dense LDLs can be changed from the rates of the same enzymes' reaction with lipoproteins other than small, dense LDLs. This change is accomplished through the use of a specific surfactant at a specific concentration, so that lipoproteins other than small, dense LDLs can be led to the outside of the reaction system. When a surfactant with a specific concentration is used in the first step of a reagent for an autoanalyzer, the rates of the enzymes' reaction with small, dense LDLs are lowered, and the reaction between the small, dense LDLs and the enzymes is delayed. Meanwhile, the above specific surfactant with a specific concentration acts on lipoproteins other than small, dense LDLs, so that such lipoproteins are caused to react with the enzymes and thus can be led to the outside of the reaction system. The present inventors have further discovered that the rates of the enzymes' reaction with lipoproteins other than small, dense LDLs increase while the reaction rate of cholesterol esterase reacting with small, dense LDLs is lowered and the enzyme reaction is delayed by specifying the concentration of the enzyme. The present inventors have succeeded in measurement of cholesterol in small, dense LDLs by leading lipoproteins other than small, dense LDLs to the outside of the reaction system in the first step as described above and then causing the remaining small, dense LDLs to react with enzymes in the second step. Thus, the present inventors have completed the present invention.

The present invention is as follows.

[1] A method for quantitatively determining cholesterol in small, dense LDLs in a sample, comprising:
a first step of eliminating lipoproteins other than small, dense LDLs in a sample in the presence of cholesterol esterase and 0.05 g/L to 1.0 g/L of a surfactant that acts on the lipoproteins other than small, dense LDLs; and
a second step of quantitatively determining cholesterol in small, dense LDLs that remain after the first step.

[2] The method for quantitatively determining cholesterol in small, dense LDLs according to [1], wherein in the first step, the surfactant that acts on lipoproteins other than small, dense LDLs is a nonionic surfactant selected from the group consisting of polyoxyethylene alkyl ether, polyoxyethylene alkyl phenyl ether, polyoxyethylene alkyl amine, and lauryl alcohol alkoxylate, an anionic surfactant selected from the group consisting of polyoxyethylene alkylether sulfate, alkyl sulfate, amide ether sulfate, alkyl taurate, and a phosphate type surfactant, a cationic surfactant selected from the group consisting of an alkyl methyl ammonium salt, a quaternary ammonium salt, and a mono-linear alkyl type surfactant, or an amphoteric surfactant selected from the group consisting of lauryl betaine, dimethyl alkyl betaine, an amide betaine type surfactant, an imidazoline type surfactant, and sodium alkyldiaminoethyl glycine.

[3] The method for quantitatively determining cholesterol in small, dense LDLs according to [1] or [2], wherein the concentration of cholesterol esterase to be used in the first step ranges from 0.6 U/mL to 3.0 U/mL.

[4] The method for quantitatively determining cholesterol in small, dense LDLs according to any one of [1] to [3], wherein cholesterol oxidase and catalase are further added in the first step.

[5] The method for quantitatively determining cholesterol in small, dense LDLs according to any one of [1] to [3], wherein cholesterol oxidase and 4 aminoantipyrine are further added in the first step.

[6] The method for quantitatively determining cholesterol in small, dense LDLs in a sample according to any one of [1] to [5], wherein an enzyme for cholesterol measurement is added in the presence of a surfactant that acts on at least small, dense LDLs in the second step.

[7] The method for quantitatively determining cholesterol in small, dense LDLs according to [6], wherein the surfactant that acts on at least small, dense LDLs, which is used in the second step, is a surfactant that acts on all lipoproteins.

[8] The method for quantitatively determining cholesterol in small, dense LDLs according to [6] or [7], wherein the surfactant that acts on at least small, dense LDLs, which is used in the second step, is a polyoxyethylene-polyoxypropylene copolymer or a derivative thereof, or a polyalkylene oxide derivative.

[9] The method for quantitatively determining cholesterol in small, dense LDLs according to any one of [6] to [8], wherein the surfactant that acts on at least small, dense LDLs, which is used in the second step, is used in the presence of lipoprotein lipase.

[10] An agent for eliminating lipoproteins other than small, dense LDLs in a sample, comprising a combination of cholesterol esterase and 0.05 g/L to 1.0 g/L of a surfactant that acts on lipoproteins other than small, dense LDLs.

[11] The agent for eliminating lipoproteins other than small, dense LDLs according to [10], wherein the concentration of cholesterol esterase ranges from 0.6 U/mL to 3.0 U/mL.

[12] A reagent for quantitatively determining small, dense LDLs, comprising a combination of cholesterol esterase, 0.05 g/L to 1.0 g/L of a surfactant that acts on lipoproteins other than small, dense LDLs and a polyoxyethylene-polyoxypropylene copolymer or a derivative thereof, or a polyalkylene oxide derivative.

[13] The reagent for quantitatively determining small, dense LDLs according to [12] comprising a first reagent composition and a second reagent composition, wherein the first reagent composition comprises cholesterol esterase and 0.05 g/L to 1.0 g/L of a surfactant that acts on lipoproteins other than small, dense LDLs and the second reagent composition comprises a polyoxyethylene-polyoxypropylene copolymer or a derivative thereof, or a polyalkylene oxide derivative.

Effect of the Invention

Through addition of a reagent containing a specific surfactant of the present invention to a sample containing lipoproteins, small, dense LDLs among lipoproteins can be directly and selectively measured without carrying out separation using a filter or centrifugation.

The description includes part or all of the contents as disclosed in the description and/or drawings of Japanese Patent Application No. 2007-49533, which is a priority document of the present application.

BEST MODE FOR CARRYING OUT THE INVENTION

Figure 1:
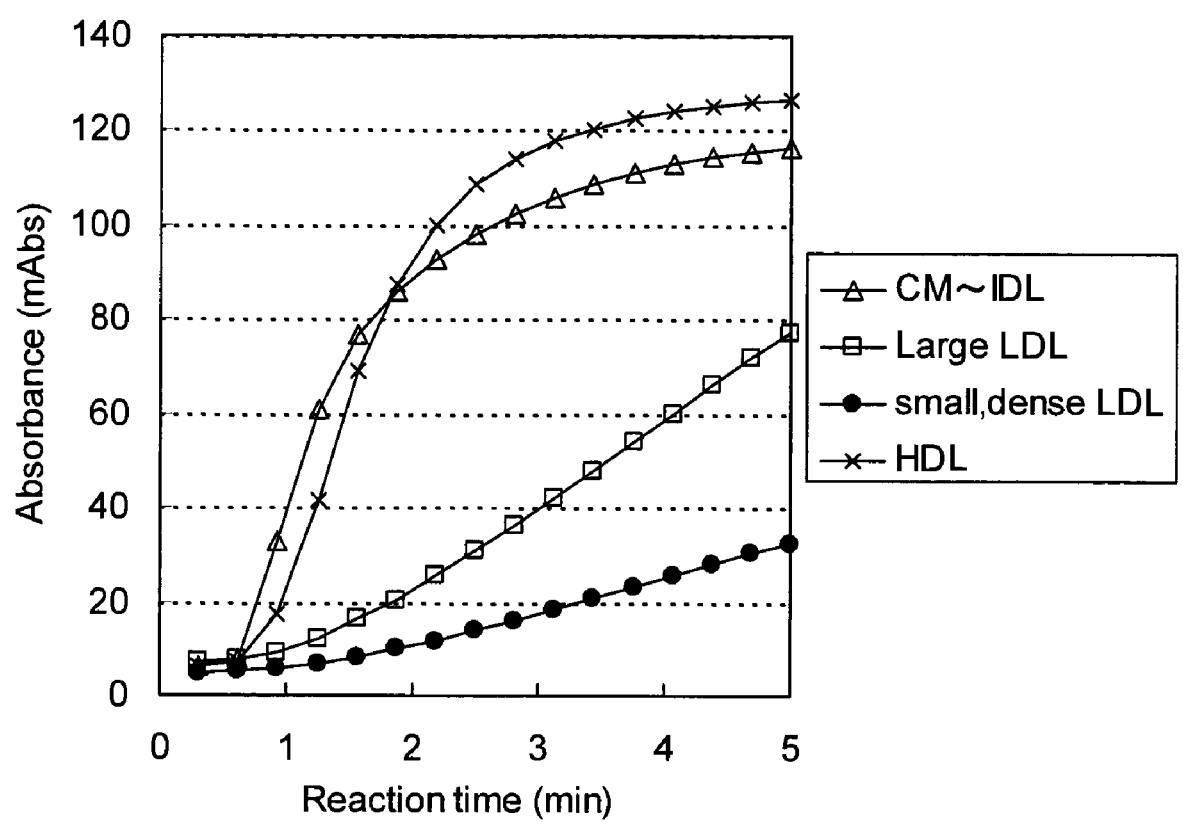
FIG. 1 shows the reactivity of each lipoprotein in a first reagent reaction in Example 1 such that cholesterol in lipoproteins other than small, dense LDLs is led to the outside of the reaction system for quantitative determination of small, dense LDL cholesterol before small, dense LDLs are caused to selectively act.

The present invention will be explained in detail as follows.
Lipoproteins can be fractionated roughly into VLDLs, LDLs, and HDLs. LDLs are further fractionated into small, dense LDLs and other sub-fractions. Small, dense LDLs are also referred to as small particle LDLs, SLDLs (small LDLs), dense LDLs, or sd LDLs. LDLs other than them may also be referred to as LLDLs (large LDLs) or light LDLs. These fractions may be distinguished from sub-fractions based on particle size or specific gravity. The particle sizes (or particle diameters) of VLDLs range from 30 nm to 80 nm (30 nm to 75 nm), those of LDLs range from 22 nm to 28 nm (19 nm to 30 nm), and those of HDLs range from 7 nm to 10 nm, although such figures may vary depending on researchers. The specific gravities of VLDLs are 1.006 or less, those of LDLs range from 1.019 to 1.063, and those of HDLs range from 1.063 to 1.21. The diameters of LDL particles can be measured by gradient gel electrophoresis (GGE) (JAMA, 260, p. 1917-21, 1988) or NMR (HANDBOOK OF LIPOPROTEIN TESTING second Edition, Edited by Nader Rifai et al. p. 609-623, AACC PRESS: The Fats of Life Summer 2002, LVDD 15 YEAR ANNIVERSARY ISSUE, Volume AVI No. 3, p. 15-16). Specific gravity can be determined based on analyses by ultracentrifugation (Atherosclerosis, 106, p. 241-253, 1994: Atherosclerosis, 83, p. 59, 1990).

Small, dense LDLs to be measured by the method of the present invention are generally sub-fractions with diameters ranging from approximately 22.0 nm to approximately 25.5 nm and specific gravities ranging from 1.040 to 1.063, among LDL fractions. The reason why LDLs are sub-fractionated based on particle size is that small LDLs among LDLs need to be fractionally measured because such LDLs with small particle sizes have a high tendency of inducing arteriosclerosis and have particularly higher malignancy than that of other LDLs. The distributions of diameter and specific gravity of LDLs are continuous. Thus, it is impossible to clearly determine that an LDL with a specific gravity that is at the aforementioned level or higher results in a particularly high degree of malignancy. Thus, the specific gravities ranging from 1.040 to 1.063 do not constitute an established characteristic of small, dense LDLs, but are values obtained by dividing the specific gravity range between 1.019 and 1.063 at the center point, a process that has been widely used and well established. For example, in another report, small, dense LDLs are fractionated in the range between 1.044 and 1.060 (Atherosclerosis: 106 241-253 1994). There are some differences among researchers on how to set the range of specific gravity for small, dense LDLs. In all cases, the presence of small, dense LDLs is associated with clinical malignancy when fractionation is performed using such specific gravity range.

In the present invention, the term "small, dense LDLs" refers to LDLs that have a low specific gravity among LDLs and clinically has a higher tendency of inducing arteriosclerosis than other LDLs. Preferably, small, dense LDLs have a specific gravity higher than the center point within the entire specific gravity range of LDLs. More preferably, small, dense LDLs have a specific gravity within the range between 1.040 and 1.063.

The method of the present invention is generally performed within an autoanalyzer. In the first step of the method of the present invention, a surfactant that acts on LDLs (hereinafter may also be referred to as large LDLs or L LDLs) other than small, dense LDLs or other lipoproteins such as VLDLs and HDLs is caused to act on a sample in the presence of cholesterol esterase, the thus generated cholesterol as a result of liberation from lipoproteins is caused to react with enzymes reacting with cholesterol in the presence of the enzymes, such as cholesterol oxidase and cholesterol dehydrogenase, so as to lead the reaction product to the outside of the reaction system. Here, the phrase "surfactant that acts on" means that a surfactant degrades lipoproteins so that cholesterol in the lipoproteins is liberated. In the case of "surfactant that acts on lipoproteins other than small, dense LDLs," such surfactant is not required to never act on small, dense LDLs, but required to act mainly on lipoproteins other than small, dense LDLs. For example, a surfactant that acts on lipoproteins other than small, dense LDLs has a lower effect on small, dense LDLs than that on lipoproteins other than small, dense LDLs.

Examples of a surfactant that reacts with LDLs (hereinafter referred to as large LDLs) other than small, dense LDLs or other lipoproteins such as VLDLs and HDLs in the first step include nonionic surfactants such as polyoxyethylene alkyl ether, polyoxyethylene alkyl phenyl ether, polyoxyethylene alkyl amine, and lauryl alcohol alkoxylate, anionic surfactants such as polyoxyethylene alkylether sulfate, alkyl sulfate, amide ether sulfate, alkyl taurate, and a phosphate type surfactant, cationic surfactants such as an alkyl methyl ammonium salt, a quaternary ammonium salt, and a monolinear alkyl type surfactant, and amphoteric surfactants such as lauryl betaine, dimethyl alkyl betaine, an amide betaine type surfactant, an imidazoline type surfactant, and sodium alkyldiaminoethyl glycine. Specific examples of the above surfactants include nonionic surfactants such as EMULGEN 120, EMULGEN 920, EMULGEN B-66, and EMULGEN A-90 (Kao Corporation), and NONION HS-220, NONION HS-215, NONION K-230, NONION NS-220, NONION NS-230, NYMEEN F-215, NYMEEN L-207, and ADEKA TOL LB-1520 (ADEKA Corporation), anionic surfactants such as EMAL 20CM, EMAL 20T, EMAL E27C, and LEV-ENOL WX (Kao Corporation), and SUNAMIDE CF-3, SUNAMIDE CF-10, DIAPON K, DIAPON F, DIAPON K-SF, PERSOFT EF, PERSOFT EFT, PERSOFT EL, PERSOFT EP, PERSOFT EK, PERSOFT SL, POLYSTAR OMP, ADEKA COL PS-440E, and TRAX K-40 (ADEKA Corporation), cationic surfactants such as QUARTAMIN 24P (Kao Corporation), ADEKA MINE MAC-30 (ADEKA Corporation), and amphoteric surfactants such as AMPHITOL 24B (Kao Corporation), NISSAN ANON LG, NISSAN ANON BDF-R, NISSAN ANON BF, NISSAN ANON BL, NISSAN ANON BL-SF, and NISSAN ANON GLM-R-LV. When such surfactant with a concentration within a specific range is used, it selectively acts on lipoproteins other than small, dense LDLs, so as to suppress the effects of cholesterol esterase on cholesterol in small, dense LDLs.

It is effective to specify the concentrations of the above surfactants for differentiation of small, dense LDLs from the other lipoproteins and selective reaction of lipoproteins other than small, dense LDLs. The concentrations of the above surfactants in the first step preferably range from 0.05 g/L to 1.0 g/L, more preferably range from 0.1 g/L to 0.8 g/L, and further preferably range from 0.3 g/L to 0.6 g/L. When the concentration of such surfactant is 1.5 g/L or more, the surfactant acts on small, dense LDLs in the first step, so as to make it difficult to differentiate small, dense LDLs from lipoproteins other than small, dense LDLs.

Cholesterol in lipoproteins resulting from the action of the surfactant and the reaction with cholesterol esterase in the first step is caused to react with cholesterol oxidase, cholesterol dehydrogenase, or the like in the presence of the enzyme. Such cholesterol can then be led to the outside of the reaction system. In the present invention, the phrase "led to the outside of the reaction system" means that cholesterol contained in HDLs, VLDLs, large LDLs or the like is eliminated, aggregated, or inhibited to avoid its reaction in the subsequent steps, for example, in order to prevent such cholesterol contained in HDLs, VLDLs, Large LDLs, or the like from affecting quantitative determination of small, dense LDL cholesterol. Small, dense LDLs alone remain in the subsequent step by leading cholesterol in large LDLs or other lipoproteins such as VLDLs and HDLs to the outside of the reaction system. In the present invention, such procedure of leading lipoproteins other than small, dense LDLs to the outside of the reaction system so as to prevent the detection of cholesterol in lipoproteins other than small, dense LDLs in the subsequent step may also be described as "differentiating small, dense LDLs from lipoproteins other than small, dense LDLs."

In the present invention, the term "elimination" refers to degrade a substance in a sample and then to prevent the degraded product from being detected in the subsequent step. That is, the phrase "eliminating lipoproteins other than small, dense LDLs in a sample in the first step" means to degrade lipoproteins other than small, dense LDLs in a sample and then to prevent the degraded product; that is, cholesterol from lipoproteins other than small, dense LDLs from being detected in the subsequent second step. Examples of a method for elimination include, but are not limited to, a method that involves degrading hydrogen peroxide (generated by causing cholesterol esterase and cholesterol oxidase to act) into water and oxygen using catalase and a method that involves causing a hydrogen donor to react with hydrogen peroxide using peroxidase, so as to perform conversion into colorless quinone.

Furthermore, lipoproteins other than small, dense LDLs can be selectively eliminated by specifying the concentration of cholesterol esterase in the presence of the above surfactant. As the concentration of cholesterol esterase contained in a reagent in the first step increases, the reactivity of particularly large LDLs (among LDLs) with the enzyme increases, leading the reaction product to the outside of the reaction system; however, the reactivity of small, dense LDLs with the enzyme does not increase. When the concentration increases further, the reactivity of small, dense LDLs with the enzyme does increase. Thus, the use of cholesterol esterase at a concentration that causes enhanced reactivity of large LDLs to the enzyme and lowered reactivity of small, dense LDLs to the enzyme makes it possible to selectively measure small, dense LDLs. Therefore, small, dense LDLs can be more selectively measured by specifying the concentration of cholesterol esterase. The concentration of cholesterol esterase in the reaction system in the first step preferably ranges from 0.6 U/mL to 3.0 U/mL, further preferably ranges from 0.9 U/mL to 2.4 U/mL, and particularly preferably ranges from 1.2 U/mL to 1.5 U/mL. Cholesterol esterase to be used in the present invention is not particularly limited, as long as it is an enzyme that hydrolyzes cholesterol ester. Animal- or microorganism-derived cholesterol esterase can be used.

Cholesterol oxidase to be used herein is not particularly limited, as long as it is an enzyme capable of oxidizing cholesterol. Animal- or microorganism-derived cholesterol oxidase can be used. The concentration of cholesterol oxidase preferably ranges from 0.01 U/mL to 20 U/mL and particularly preferably ranges from 0.1 U/mL to 1 U/mL.

Cholesterol dehydrogenase to be used herein is not particularly limited, as long as it is an enzyme capable of oxidizing cholesterol so as to reduce the oxidized coenzyme. Animal- or microorganism-derived cholesterol dehydrogenase can be used. The concentration of cholesterol dehydrogenase preferably ranges from 0.01 U/mL to 200 U/mL and particularly preferably ranges from 0.1 U/mL to 100 U/mL.

In addition, lipoproteinase can also be added arbitrarily to a reaction solution in the first step in order to adjust the effects on various lipoproteins. As such lipoproteinase, phospholipase and/or lipoprotein lipase can be used.

As phospholipase, phospholipase A2, phospholipase C, phospholipase D, lysophospholipase, or the like can be used at a concentration preferably ranging from 0.01 U/mL to 10 U/mL, further preferably ranging from 0.01 U/mL to 5 U/mL, and particularly preferably ranging from 0.01 U/mL to 1 U/mL.

Lipoprotein lipase to be used herein is not particularly limited, as long as it is an enzyme capable of degrading lipoproteins. Animal- or microorganism-derived lipoprotein lipase can be used. The concentration of such lipoprotein lipase, which is employed herein, preferably ranges from 0.01 U/mL to 10 U/mL, further preferably ranges from 0.01 U/mL to 5 U/mL, and particularly preferably ranges from 0.01 U/mL to 1 U/mL.

In the second step of the present invention, the amount of cholesterol in small, dense LDLs that has not reacted in the first step is quantitatively determined. To quantitatively determine cholesterol in small, dense LDLs, which has remained unreacted in the first step, a conventional method for quantitatively determining LDLs can be employed. Examples of such method include a method that involves adding an LDL coagulant and then quantitatively determining the content of the thus formed LDL-specific aggregates by turbidimetric determination, a method that involves an antigen-antibody reaction with an LDL-specific antibody, and a method that involves quantitatively determining degraded products using enzymes. Of these methods, a method that is preferred herein involves adding an enzyme for cholesterol measurement, such as cholesterol esterase, cholesterol oxidase, or cholesterol dehydrogenase and then quantitatively determining the reaction product. A surfactant that acts on at least small, dense LDLs is used for quantitative determination of cholesterol in small, dense LDLs. Such surfactant that acts on at least small, dense LDLs may be a surfactant that acts on only small, dense LDLs, a surfactant that acts also on other lipoproteins in addition to small, dense LDLs, or a surfactant that acts on all lipoproteins.

As a surfactant that reacts with small, dense LDLs, a polyoxyethylene-polyoxypropylene copolymer or a derivative thereof can be appropriately used. Examples of the polyoxyethylene-polyoxypropylene copolymer or a derivative thereof include Pluronic (trademark)-based surfactants (e.g., BASF and ADEKA Corporation) such as Pluronic 17R-4, Pluronic L-64, Pluronic PE3100, Pluronic P-85, Pluronic F-88, Pluronic P-103, and Pluronic F-127.

As a surfactant that acts on all lipoproteins, any surfactant can be used as long as it is used in reagents or the like for total cholesterol measurement. A preferred example of such surfactant is a polyalkylene oxide derivative with HLB of 11 or more and less than 13 and preferably with HLB of 12 or more and less than 13.

Furthermore, the surfactant that reacts with LDLs other than small, dense LDLs (hereafter, referred to as large LDLs) or other lipoproteins, such as VLDLs and HDLs, may be used at a given concentration or higher: for example, 1.5 g/L or more.

The concentration of a surfactant to be used in the second step preferably ranges from approximately 0.1 g/L to 100 g/L and further preferably ranges from approximately 1 g/L to 50 g/L.

When cholesterol esterase and cholesterol oxidase are used as enzymes (reacting with cholesterol) for cholesterol measurement, hydrogen peroxide is generated by the enzyme reaction. The thus generated hydrogen peroxide can be quantitatively determined through measurement at a wavelength between 400 nm and 700 nm using a dye (colored quinone) that is formed by the coupling reaction of a hydrogen donor with a hydrogen receptor in the presence of peroxidase.

As a hydrogen donor, an aniline derivative is preferred. Examples of such aniline derivative include N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(3-sulfopropyl)-3-methylaniline (TOPS), N-(2-hydroxy-3-sulfopropyl)-3,5-dimethoxyaniline (HDAOS), N-(3-sulfopropyl)aniline (HALPS), and N-(3-sulfopropyl)-3-methoxy-5-aniline (HMMPS). The concentration of such hydrogen donor, which is employed herein, preferably ranges from 0.1 mmol/L to 1.5 mmol/L at a final concentration.

As a hydrogen receptor, 4-aminoantipyrine, methylbenzothiazolonhydrazone, or the like can be used.

When cholesterol esterase and cholesterol dehydrogenase are used as enzymes for cholesterol measurement, NAD(P)H is generated from NAD(P) by the enzyme reaction. The thus generated NAD(P)H can be quantitatively determined by measuring absorbance at 330 nm to 400 nm.

In the present invention, a monovalent cation and/or a divalent cation or a salt thereof can be used as an ionic strength adjuster. Addition of such ionic strength adjuster facilitates differentiation of small, dense LDLs from large LDLs. Specifically, sodium chloride, potassium chloride, magnesium chloride, manganese chloride, calcium chloride, lithium chloride, ammonium chloride, magnesium sulfate, potassium sulfate, lithium sulfate, ammonium sulfate, magnesium acetate, and the like can be used. The concentration employed herein ranges from 0 mmol/L to 100 mmol/L.

The reaction is preferably performed within a temperature range between 2° C. and 45° C. and further preferably between 25° C. and 40° C.

The reaction is preferably performed for 1 to 30 minutes and more preferably for 3 to 15 minutes.

Serum and blood plasma can be used as samples in the present invention. However, examples thereof are not limited thereto.

Examples of an autoanalyzer to be used in the present invention include TBA-120FR.200FR (Toshiba), JCA-BM1250 1650-2250 (JEOL Ltd.), HITACHI 7180-7700 (Hitachi), and AU2700 (OLYMPUS).

When the measurement method of the present invention is performed, reagents to be used herein may be divided into a plurality of reagent compositions. Examples of reagents to be used in the present invention include surfactants that react with LDLs other than small, dense LDLs or other lipoproteins such as VLDLs and HDLs, a polyoxyethylene-polyoxypropylene copolymer or a derivative thereof, enzymes for cholesterol measurement, such as cholesterol esterase and cholesterol oxidase, surfactants, catalase that degrades hydrogen peroxide, peroxidase for the formation of a dye from hydrogen peroxide via coupling reaction, a hydrogen donor, and a buffer. Division of these reagents into different reagent compositions is adequately performed in view of stability and the like of the reagents. For example, reagents are divided into two compositions: a first reagent composition; and a second reagent composition. The first reagent composition can comprise a surfactant that reacts with LDLs other than small, dense LDLs or other lipoproteins such as VLDLs and HDLs, enzymes for cholesterol measurement, such as cholesterol esterase and cholesterol oxidase, and the like and the second reagent composition can comprise a surfactant that reacts with small, dense LDLs or a surfactant that reacts with all lipoproteins, such as a polyoxyethylene-polyoxypropylene copolymer or a derivative thereof, a surfactant for enhancement of the activity of such enzymes for cholesterol measurement, and the like. The second reagent composition may further comprise phospholipase or lipoprotein lipase. When such two reagent compositions are used, the first reagent composition is added to a sample, followed by 1 to 10 minutes and preferably approximately 5 minutes of reaction. The second reagent composition is then added, followed by further 1 to 10 minutes and preferably approximately 5 minutes of reaction. The thus formed dye can be quantitatively determined. In this case, the first step comprises adding the first reagent composition to cause LDLs other than small, dense LDLs (hereinafter referred to as large LDLs) or other lipoproteins such as VLDLs and HDLs to act on a surfactant for reaction with the enzymes. The second step comprises adding the second reagent composition to cause small, dense LDLs to act on a surfactant for reaction with the enzymes and then measuring cholesterol in small, dense LDLs.

EXAMPLES

Hereafter, the present invention is described in greater detail with reference to the following examples, although the present invention is not limited thereto.

Example 1

The first reagent composition having the following composition was prepared as an example of a reagent containing a surfactant acting on lipoproteins other than small, dense LDLs.
First Reagent Composition

| | |
|---|---|
| PIPES buffer (pH 7.0) | 50 mmol/L |
| Cholesterol esterase | 0.6 U/mL |
| Cholesterol oxidase | 0.5 U/mL |
| Polyoxyethylene-distyrene phenyl ether EMULGEN A-90 | 0.3 g/L |
| Bovine serum albumin | 0.5% |
| TOOS | 2.0 mmol/L |
| 4-aminoantipyrine | 4.0 mmol/L |
| Peroxidase | 12.0 unit/mL |

In the above reagent composition, EMULGEN A-90 (polyoxyethylene-distyrene phenyl ether) is a surfactant that acts on lipoproteins other than small, dense LDLs.

In this Example, to reveal that cholesterol in lipoproteins other than small, dense LDLs was led to the outside of the reaction system for quantitative determination by the use of the first reagent composition, components required for quinone dye formation, such as chromogenic substrates, TOOS and 4-aminoantipyrine, and peroxidase enzyme were added to the first reagent composition and then absorbance was measured. Hence, in this Example, the reaction state of the small, dense LDL reagent in the first step of the measurement method of the present invention was confirmed.

The first reagent (300 mL) was added to 4 µL each of a chylomicron-IDL fraction, a small, dense LDL fraction, a fraction of LDLs other than small, dense LDLs, and an HDL fraction, each having a cholesterol content of 100 mg/dL separated by an ultracentrifugation method, followed by 5 minutes of reaction at 37° C. Absorbance (reaction time course) at each time point was measured.

FIG. 1 shows the results.

As shown in FIG. 1, in this Example, the reaction composition exhibited high reactivity to the chylomicron-IDL fraction, the fraction of LDLs other than small, dense LDLs (large LDLs), and the HDL fraction within the first 5 minutes in the reaction solutions because of the action of the surfactant, but exhibited low reactivity to small, dense LDLs. When quantitative determination of small, dense LDL cholesterol is performed, in the first step that is a preliminary step for the reaction for selective action on small, dense LDLs, lipoproteins other than small, dense LDLs are caused to react in advance with enzymes through the use of the surfactant (used in this Example) together with enzymes and the like reacting with cholesterol. This makes it possible to eliminate the cholesterol and lead it to the outside of the reaction system.

Example 2

The first and second reagent compositions were prepared, each containing in the first reagent composition a surfactant acting on lipoproteins other than small, dense LDLs and having a composition shown below.
First Reagent Composition

| | |
|---|---|
| PIPES buffer (pH 7.0) | 50 mmol/L |
| Cholesterol esterase [Asahi Kasei Corporation] | 0.6 U/mL |
| Cholesterol oxidase [Toyobo] | 0.5 U/mL |
| Catalase | 600 U/mL |
| Polyoxyethylene benzyl phenyl ether | 0-1.2 g/L |
| Bovine serum albumin | 1.0% |
| TOOS | 2.0 mmol/L |

Second Reagent Composition

| | |
|---|---|
| PIPES buffer (pH 7.0) | 50 mmol/L |
| Polyoxyethylene alkylphenyl ether | 10 g/L |
| 4-aminoantipyrine | 4.0 mmol/L |
| Peroxidase | 4.0 unit/mL |
| Sodium azide | 0.05% |

In the first reagent composition, the surfactant polyoxyethylene benzyl phenyl ether acts on lipoproteins other than small, dense LDLs. Whether polyoxyethylene benzyl phenyl ether used at a concentration ranging from 0 g/L to 1.2 g/L acted on small, dense LDLs at each concentration was confirmed.

Furthermore, in the second reagent composition, polyoxyethylene alkyl phenyl ether contained at a concentration as high as 10 g/L acts on small, dense LDLs.

The first reagent composition (300 µL) was added to a small, dense LDL fraction or a large LDL fraction with a cholesterol content of 100 mg/dL separated by an ultracentrifugation method, followed by 5 minutes of reaction at 37° C. (first step). After the first step, 100 µL of the second reagent composition was added, followed by 5 minutes of reaction (second step) and then absorbance was measured at 600 nm. LDL-EX N "SEIKEN" was used as a control reagent reacting with both small, dense LDLs and large LDLs.

Figure 2:
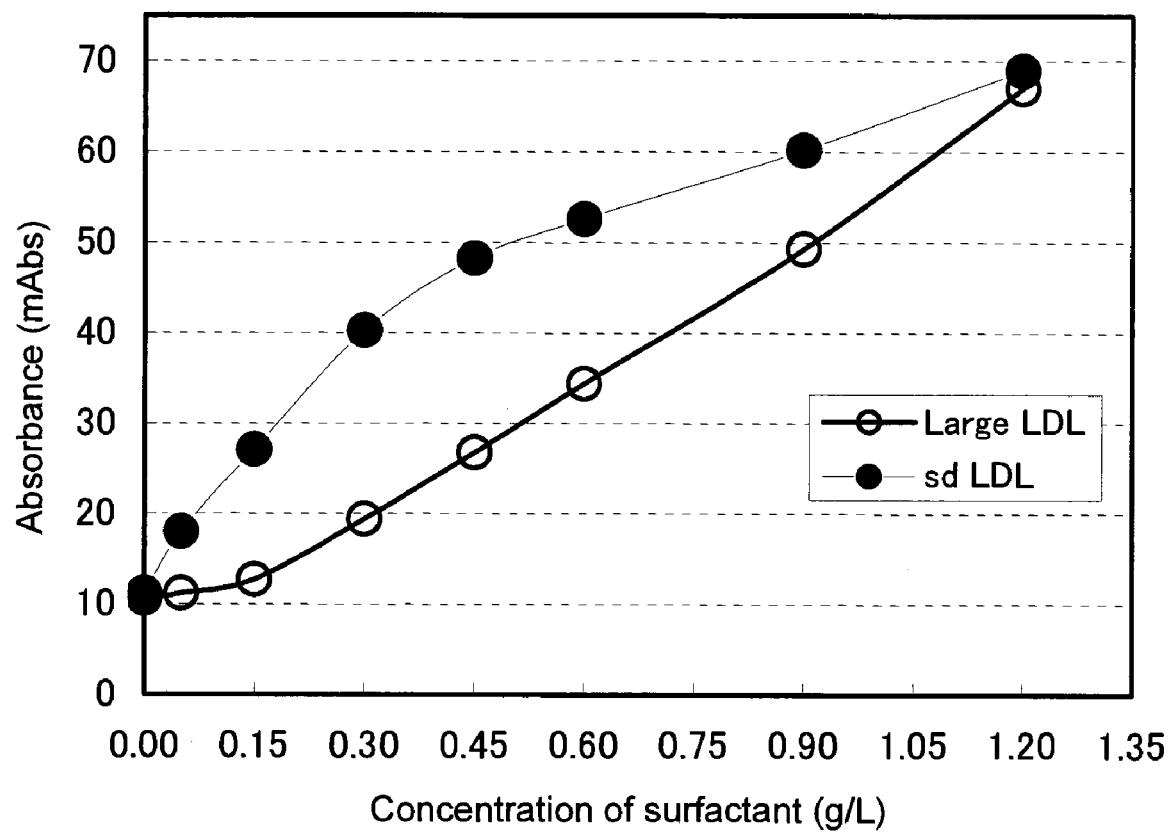
FIG. 2 shows the reactivity of sd LDLs and large LDLs with respect to the concentration of the surfactant in the first step.

FIG. 2 shows the results.

When a surfactant was added at a low concentration (FIG. 2), the resulting absorbance of small, dense LDLs was higher than that of large LDLs. As the concentration of the surfactant increased, the absorbance of large LDLs also increased, and the difference in the amount of small, dense LDLs that were absorbed and the amount of large LDLs that were absorbed decreased. This result suggests that, when the concentration of a surfactant is low, lipoproteins other than small, dense LDLs are led to the outside of the reaction system in the first step, allowing small, dense LDLs to be measured precisely. As described in Example 1, when a surfactant is used at a low concentration in the first step of the method of the present invention, large LDLs are selectively eliminated and then led to the outside of the reaction system, but small, dense LDLs are not. As the concentration of the surfactant increases, the amount of large LDLs eliminated decreases until it is equivalent to that of small, dense LDLs. As a result, the cholesterol in small, dense LDLs can be selectively measured through the use of a surfactant at a concentration, preferably ranging from 0.05 g/L to 0.9 g/L, and more preferably ranging from 0.3 g/L to 0.6 g/L in the first step.

Example 3

The first and second reagent compositions were prepared, containing various surfactants acting on lipoproteins other than small, dense LDLs in the first reagent composition and having the following compositions.

First Reagent Composition

| | |
|---|---|
| PIPES buffer (pH 7.0) | 50 mmol/L |
| Cholesterol esterase [Asahi Kasei Corporation] | 1.2 U/mL |
| Cholesterol oxidase [Toyobo] | 0.5 U/mL |
| Catalase | 600 U/mL |
| Various surfactants | 0.3 g/L or 0.6 g/L |
| Bovine serum albumin | 1.0% |
| TOOS | 2.0 mmol/L |

Second Reagent Composition

| | |
|---|---|
| PIPES buffer (pH 7.0) | 50 mmol/L |
| Polyoxyethylene alkylphenyl ether | 10 g/L |
| 4-aminoantipyrine | 4.0 mmol/L |
| Peroxidase | 4.0 unit/mL |
| Sodium azide | 0.05% |

The first reagent composition (300 μL) was added to a small, dense LDL fraction or a large LDL fraction with a cholesterol content of 100 mg/dL separated by an ultracentrifugation method, followed by 5 minutes of reaction at 37° C. (first step). After the first step, 100 μL of the second reagent composition was added, followed by 5 minutes of reaction (second step) and then absorbance was measured at 600 nm. LDL-EX N "SEIKEN" was used as a control reagent reacting with both small, dense LDLs and Large LDLs.

The various surfactants that were contained in the first reagent composition and the results are shown in Table 1. When a surfactant specifically acted on large LDLs and was then led to the outside of the reaction system in the first step, the absorbance of large LDLs decreased as shown in Table 1. Moreover, when a surfactant did not act on small, dense LDLs in the first step, the absorbance of small, dense LDLs increased as shown in Table 1.

As shown in Table 1, surfactants used in this Example specifically acted on large LDLs in the first step, leading large 1 LDLs to the outside of the reaction system, so that small, dense LDLs were selectively measured.

Table 1 shows the reactivity to small, dense LDLs or large LDLs when various surfactants were used.

TABLE 1

| | Concentration of surfactant (g/L) in the first step | Small, dense LDL (mAbs) | Large LDL (mAbs) | sdLDL/L LDL % | Composition |
|---|---|---|---|---|---|
| LDL-EX N | — | 71.5 | 71.6 | 100% | |
| EMULGEN 120 | 0.3 | 58.8 | 41.2 | 143% | Polyoxyethylene lauryl ether |
| EMULGEN 920 | 0.3 | 37.8 | 18.8 | 201% | Polyoxyethylene nonylphenyl ether |
| EMULGEN B66 | 0.3 | 34.9 | 14.2 | 246% | Polyoxyethylene tri-benzyl phenyl ether |
| EMULGEN A90 | 0.3 | 57.8 | 31.5 | 183% | Polyoxyethylene-distyrene phenyl ether |
| NONION HS215 | 0.3 | 33.8 | 17.6 | 192% | Polyoxyethylene octylphenyl ether |
| NONION HS-220 | 0.6 | 55.7 | 32.6 | 171% | Polyoxyethylene octylphenyl ether |
| NONION K230 | 0.3 | 56.9 | 41.7 | 136% | Polyoxyethylene lauryl ether |
| NONION NS220 | 0.3 | 34.5 | 18.0 | 192% | Polyoxyethylenenonylphenyl ether |
| NONION NS230 | 0.6 | 62.0 | 40.3 | 154% | Polyoxyethylenenonylphenyl ether |
| NYMEEN L-207 | 0.3 | 62.9 | 51.6 | 122% | Polyoxyethylenedodecylamine |
| NYMEEN F215 | 0.3 | 61.1 | 47.0 | 130% | Polyoxyethylene alkyl amine |
| ADEKA TOL LB-1520 | 0.3 | 78.5 | 65.9 | 119% | Lauryl alcohol alkoxylate |
| EMAL 20CM | 0.6 | 27.5 | 18.1 | 152% | Sodium polyoxyethylene alkyl ether sulfate |
| EMAL 20T | 0.6 | 36.0 | 24.4 | 148% | Triethanolamine polyoxyethylene alkyl ether sulfate |
| EMAL E27C | 0.6 | 26.8 | 19.0 | 141% | Sodium polyoxyethylene lauryl ether sulfate |
| LEVENOL WX | 0.3 | 19.1 | 12.2 | 157% | Sodium polyoxyethylene alkyl ether sulfate |
| SUNAMIDE C-3 | 0.6 | 29.6 | 20.3 | 146% | Amide ether sulfate |
| SUNAMIDE CF-10 | 0.6 | 36.5 | 24.2 | 151% | Amide ether sulfate |
| SUNAMIDE CF-3 | 0.3 | 18.5 | 12.5 | 148% | Amide ether sulfate |
| DIAPON K | 0.6 | 45.2 | 34.3 | 132% | Sodium acyl methyl taurate |
| DIAPON F | 0.3 | 19.3 | 15.2 | 127% | Sodium acyl methyl taurate |
| DIAPON K-SF | 0.3 | 14.7 | 11.0 | 134% | Sodium acyl methyl taurate |
| PERSOFT EF | 0.6 | 29.3 | 20.7 | 142% | Alkyl ether sulfate |
| PERSOFT EFT | 0.6 | 39.1 | 28.9 | 135% | Alkyl ether sulfate |
| PERSOFT EL | 0.3 | 25.6 | 17.4 | 147% | Alkyl ether sulfate |
| PERSOFT EP | 0.6 | 31.0 | 21.4 | 145% | Alkyl ether sulfate |
| PERSOFT EK | 0.3 | 21.9 | 15.4 | 142% | Alkyl ether sulfate |
| PERSOFT SL | 0.6 | 43.2 | 32.4 | 133% | Alkyl sulfate |
| POLYSTAR OMP | 0.3 | 41.6 | 31.2 | 133% | High molecular type anion |
| ADEKA COL PS-440E | 0.3 | 56.2 | 27.1 | 207% | Aliphatic phosphoric acid ester |
| TRAX K-40 | 0.3 | 18.6 | 13.6 | 137% | Special anion |
| QUARTAMIN 24P | 0.6 | 60.8 | 43.8 | 139% | Lauryl trimethyl ammonium chloride |

TABLE 1-continued

| | Concentration of surfactant (g/L) in the first step | Small, dense LDL (mAbs) | Large LDL (mAbs) | sdLDL/L LDL % | Composition |
|---|---|---|---|---|---|
| ADEKA MINE 4MAC-30 | 0.6 | 57.2 | 44.4 | 129% | Mono-linear alkyl type |
| AMPHITOL 24B | 0.3 | 65.1 | 51.1 | 127% | Lauryl betaine |
| NISSAN ANON LG | 0.6 | 58.9 | 38.7 | 152% | Sodium lauryl diaminoethylglycine |
| NISSAN ANON BDF-R | 0.3 | 23.0 | 16.7 | 138% | Amide betaine type |
| NISSAN ANON BF | 0.3 | 62.3 | 48.6 | 128% | Dimethyl alkyl betaine |
| NISSAN ANON BL | 0.3 | 56.0 | 45.2 | 124% | Dimethyl alkyl betaine |
| NISSAN ANON BL-SF | 0.3 | 64.6 | 54.2 | 119% | Dimethyl alkyl betaine |
| NISSAN ANON GLM-R-LV | 0.6 | 25.0 | 14.7 | 170% | Imidazoline type |

Example 4

The following reagent compositions with varied cholesterol esterase enzyme activity (enzyme concentration) to be caused to act on lipoproteins were prepared.
First Reagent Composition

| PIPES buffer (pH 7.0) | 50 mmol/L |
| Cholesterol esterase [Asahi Kasei Corporation] | 0.6-3.0 U/mL |
| Cholesterol oxidase [Toyobo] | 0.5 U/mL |
| Catalase | 600 U/mL |
| Polyoxyethylene-distyrene phenyl ether [Kao Corporation] | 0.03% |
| Bovine serum albumin | 0.5% |
| TOOS | 2.0 mmol/L |

Second Reagent Composition

| PIPES buffer (pH 7.0) | 50 mmol/L |
| Polyoxyethylene-polyoxypropylene copolymer Pluronic 17R-4 [ADEKA Corporation] | 0.3% |
| 4-aminoantipyrine | 4.0 mmol/L |
| Peroxidase | 4.0 unit/mL |
| Sodium azide | 0.05% |

The first reagent (300 µL) was added to 4 µL each of a small, dense LDL fraction or a large LDL fraction with a cholesterol content of 100 mg/dL separated by an ultracentrifugation method, followed by 5 minutes of reaction at 37° C. After reaction, 100 µL of the second reagent was added, followed by 5 minutes of reaction and then absorbance was measured at 600 nm.

Figure 3:
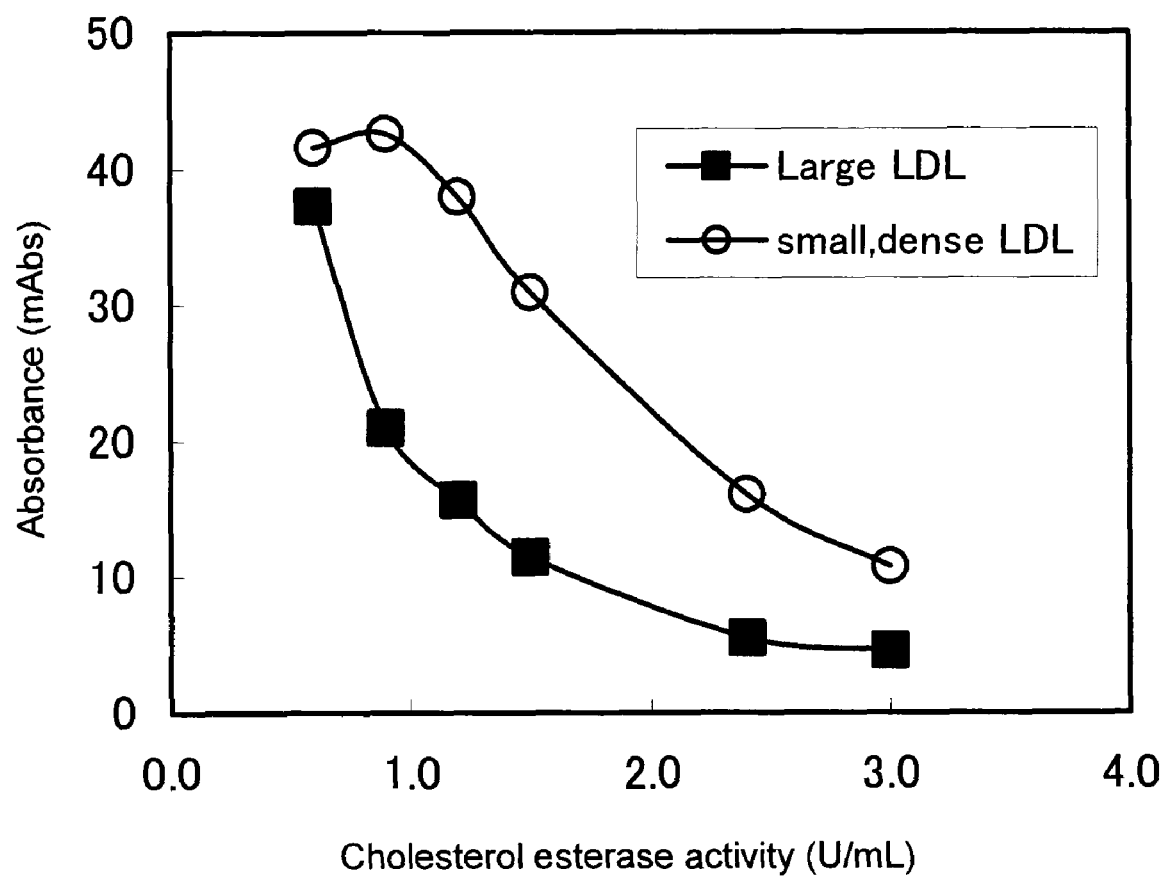
FIG. 3 shows the reactivity to large LDLs and small, dense LDLs when the activity of the cholesterol esterase is varied.

FIG. 3 shows the results.

As shown in FIG. 3, as the activity of cholesterol esterase in the reagent increased, the absorbance of large LDLs first decreased; however, as the activity of cholesterol esterase increased further, the absorbance of small, dense LDLs decreased later. Accordingly, cholesterol in small, dense LDLs can be efficiently measured by specifying an appropriate concentration of cholesterol esterase. Cholesterol in small, dense LDLs can be selectively measured using cholesterol esterase at a concentration, preferably ranging from 0.6 U/mL to 3.0 U/mL, more preferably ranging from 0.9 U/mL to 2.4 U/mL, and further preferably ranging from 0.9 U/mL to 1.5 U/mL in the first step.

All publications, patents, and patent applications cited herein are incorporated herein by reference in their entirety.

The invention claimed is:

1. A method for quantitatively determining cholesterol in small, dense LDLs in a sample selectively, comprising:
   a first step of eliminating lipoproteins other than small, dense LDLs in a sample in the presence of cholesterol esterase and 0.05 g/L to 1.0 g/L of a surfactant that degrades the lipoproteins other than small, dense LDLs; and
   a second step of quantitatively determining cholesterol selectively in small, dense LDLs that remain after the first step.

2. The method for quantitatively determining cholesterol in small, dense LDLs selectively according to claim 1, wherein in the first step, the surfactant that degrades lipoproteins other than small, dense LDLs is a nonionic surfactant selected from the group consisting of polyoxyethylene alkyl, ether, polyoxyethylene alkyl phenyl ether, polyoxyethylene alkyl amine, and lauryl alcohol alkoxylate, an anionic surfactant selected from the group consisting of polyoxyethylene alkylether sulfate, alkyl sulfate, amide ether sulfate, alkyl taurate, and a phosphate type surfactant, a cationic surfactant selected from the group consisting of an alkyl methyl ammonium salt, a quaternary ammonium salt, and a mono-linear alkyl type surfactant, or an amphoteric surfactant selected from the group consisting of lauryl betaine, dimethyl alkyl betaine, an amide betaine type surfactant, an imidazoline type surfactant, and sodium alkyldiamioethyl glycine.

3. The method of quantitatively determining cholesterol in small, dense LDLs selectively according to claim 1, wherein the concentration of cholesterol esterase to be used in the first step ranges form 0.6 U/mL to 3.0 U/mL.

4. The method of quantitatively determining cholesterol in small, dense LDLs selectively according to claim 1, wherein cholesterol oxidase and catalase are further added in the first step.

5. The method of quantitatively determining cholesterol in small, dense LDLs selectively according to claim 1, wherein cholesterol oxidase and 4 aminoantipyrine are further added in the first step.

6. The method of quantitatively determining cholesterol in small, dense LDLs in a sample selectively according to claim 1, wherein an enzyme for cholesterol measurement is added in the presence of a surfactant that degrades at least small, dense LDLs in the second step.

7. The method for quantitatively determining cholesterol in small, dense LDLs selectively according to claim 6, wherein the surfactant that degrades at least small, dense LDLs, which are used in the second step, is a surfactant that degrades all lipoproteins.

8. The method for quantitatively determining cholesterol in small, dense LDLs selectively according to claim 6, wherein the surfactant that degrades at least small, dense LDLs, which is used in the second step, is a polyoxyethylene-polyoxypropylene copolymer or a derivative thereof, or a polyalkylene oxide derivative.

9. The method for quantitatively determining cholesterol in small, dense LDLs selectively according to claim 6, wherein the surfactant that degrades at least small, dense LDLs, which is used in the second step, is used in the presence of lipoprotein lipase.

10. The method for quantitatively determining cholesterol in small, dense LDLs selectively according to claim 1, wherein 0.05 g/L to 0.8 g/L of the surfactant is used in the first step.

* * * * *